United States Patent
Chae et al.

(10) Patent No.: US 11,696,713 B2
(45) Date of Patent: Jul. 11, 2023

(54) CONTOUR ELECTROCORTICOGRAPHY (ECOG) ARRAY

(71) Applicants: Arizona Board of Regents on behalf of Arizona State University, Scottsdale, AZ (US); Mayo Foundation for Medical Education and Research, Rochester, MN (US)

(72) Inventors: Junseok Chae, Scottsdale, AZ (US); Shiyi Liu, Asu, AZ (US); Alfredo Quinones-Hinojosa, Rochester, MN (US); Tito Vivas-Buitrago, Rochester, MN (US)

(73) Assignees: Arizona Board of Regents on behalf of Arizona State University, Scottsdale, AZ (US); Mayo Foundation for Medical Education and REsearch, Rochester, MN (US)

( * ) Notice: Subject to any disclaimer, the term of this patent is extended or adjusted under 35 U.S.C. 154(b) by 507 days.

(21) Appl. No.: 16/809,778

(22) Filed: Mar. 5, 2020

(65) Prior Publication Data
US 2020/0289002 A1 Sep. 17, 2020

Related U.S. Application Data

(60) Provisional application No. 62/819,042, filed on Mar. 15, 2019.

(51) Int. Cl.
*A61B 5/24* (2021.01)
*A61B 5/00* (2006.01)

(52) U.S. Cl.
CPC .............. *A61B 5/24* (2021.01); *A61B 5/0031* (2013.01); *A61B 5/6868* (2013.01); *A61B 2562/046* (2013.01)

(58) Field of Classification Search
CPC ......... A61B 5/0031; A61B 5/046; A61B 5/24; A61B 5/6868
See application file for complete search history.

(56) References Cited

U.S. PATENT DOCUMENTS

| 4,033,357 A | 7/1977 | Helland et al. |
| 4,041,954 A | 8/1977 | Ohara |
| (Continued) | | |

FOREIGN PATENT DOCUMENTS

| WO | WO2009064577 A1 | 5/2009 |
| WO | WO2010088219 A2 | 8/2010 |
| (Continued) | | |

OTHER PUBLICATIONS

I. Blumcke et al., Histopathological Finding in Brain Tissue Obtained during Epilepsy Surgery, New England Journal of Medicine, 2017, pp. 1648-1656, vol. 377.

(Continued)

*Primary Examiner* — Christopher A Flory
(74) *Attorney, Agent, or Firm* — Riverside Law LLP

(57) ABSTRACT

ElectroCorticoGraphy (ECoG) sensors and uses are disclosed. These ECoG arrays, systems, and processes may be operable or configured to: i) simultaneously record neural signals while providing stimulation on specific portions of the cortex using a user-guided stimulator; ii) acquire neural signals over a large cortex area; iii) provide individual or group stimulation while concurrently receiving neural feedback; and/or iv) acquire neural signals at a setting remote from the neural source using wireless or other communication techniques.

18 Claims, 5 Drawing Sheets

(56) References Cited

U.S. PATENT DOCUMENTS

| | | | |
|---|---|---|---|
| 6,790,178 | B1 | 9/2004 | Mault et al. |
| 6,871,084 | B1 | 3/2005 | Kingsley et al. |
| 6,889,086 | B2 | 5/2005 | Mass et al. |
| 8,019,419 | B1 | 9/2011 | Panescu et al. |
| 8,129,622 | B2 | 3/2012 | Taylor et al. |
| 8,321,021 | B2 | 11/2012 | Kisker et al. |
| 8,345,910 | B2 | 1/2013 | Chae et al. |
| 8,725,270 | B2 | 5/2014 | Towe |
| 8,909,343 | B2 | 12/2014 | Towe |
| 8,923,963 | B2 | 12/2014 | Bonner et al. |
| 9,168,383 | B2 | 10/2015 | Jacobson et al. |
| 9,358,136 | B2 | 6/2016 | Stein et al. |
| 9,409,029 | B2 | 8/2016 | Perryman et al. |
| 9,446,255 | B2 | 11/2016 | Towe et al. |
| 9,623,253 | B2 | 4/2017 | Perryman et al. |
| 9,693,708 | B2 | 7/2017 | Towe |
| 9,700,712 | B2 | 7/2017 | Towe |
| 9,935,498 | B2 | 4/2018 | Joshi |
| 10,119,960 | B2 | 11/2018 | Chae et al. |
| 10,576,305 | B2 | 3/2020 | Maharbiz et al. |
| 11,000,257 | B2 | 5/2021 | Adler et al. |
| 2006/0020224 | A1 | 1/2006 | Geiger |
| 2006/0235484 | A1 | 10/2006 | Jaax et al. |
| 2008/0183247 | A1 | 7/2008 | Harding |
| 2008/0275356 | A1 | 11/2008 | Stasz et al. |
| 2009/0204170 | A1 | 8/2009 | Hastings et al. |
| 2009/0299216 | A1 | 12/2009 | Chen et al. |
| 2010/0016762 | A1 | 1/2010 | Thapliyal et al. |
| 2010/0198039 | A1 | 8/2010 | Towe |
| 2010/0324378 | A1 | 12/2010 | Tran et al. |
| 2011/0004076 | A1 | 1/2011 | Janna et al. |
| 2011/0054583 | A1* | 3/2011 | Litt ............... A61N 1/0553 600/377 |
| 2012/0296444 | A1* | 11/2012 | Greenberg ....... A61N 1/0531 607/152 |
| 2013/0018440 | A1 | 1/2013 | Chow et al. |
| 2013/0261703 | A1 | 10/2013 | Chow et al. |
| 2014/0276048 | A1 | 9/2014 | Kiley et al. |
| 2014/0277258 | A1* | 9/2014 | Mercanzini ....... A61N 1/37211 607/45 |
| 2014/0350348 | A1 | 11/2014 | Tee et al. |
| 2016/0017268 | A1 | 1/2016 | Kim et al. |
| 2016/0030757 | A1 | 2/2016 | Jacobson |
| 2016/0367186 | A1 | 12/2016 | Freeman et al. |
| 2017/0086686 | A1* | 3/2017 | Narasimhan ....... A61B 5/02141 |
| 2017/0095198 | A1 | 4/2017 | Towe |
| 2017/0128015 | A1* | 5/2017 | Rogers ............. A61B 5/291 |
| 2017/0209094 | A1 | 7/2017 | Derchak et al. |
| 2018/0093092 | A1* | 4/2018 | Howard ............. A61N 1/0529 |
| 2018/0192941 | A1 | 7/2018 | Annoni et al. |
| 2018/0358119 | A1 | 12/2018 | Bhushan et al. |
| 2019/0021692 | A1 | 1/2019 | Utsugida et al. |
| 2019/0223782 | A1 | 7/2019 | Wen et al. |
| 2019/0229770 | A1 | 7/2019 | Khaleghi et al. |
| 2019/0254565 | A1 | 8/2019 | Toth et al. |
| 2020/0001089 | A1 | 1/2020 | Chae |
| 2020/0253578 | A1 | 8/2020 | Chae et al. |
| 2020/0309612 | A1 | 10/2020 | Liu et al. |
| 2021/0052225 | A1 | 2/2021 | Shetty et al. |
| 2021/0267523 | A1* | 9/2021 | Donoghue ........ A61N 1/0504 |

FOREIGN PATENT DOCUMENTS

| | | |
|---|---|---|
| WO | WO2014144219 A1 | 9/2014 |
| WO | WO2015191600 A1 | 12/2015 |
| WO | 2018011235 A1 | 1/2018 |

OTHER PUBLICATIONS

P. Kwan et al., Erratum-Definition of drug resistant epilepsy: consensus proposal by the ad hoc Task Force of the ILAE Commission on Therapeutic Strategic, Epilepsia, Sep. 2010, pp. 1922, vol. 51 issue 9.

P. Kwan et al., Definition of drug resistant epilepsy: consensus proposal by the ad hoc Task Force of the ILAE Commission on Therapeutic Strategies, Epilepsia, Jun. 2010, pp. 1069-1077, vol. 51 issue 6.

P. Kwan et al., Early identification of refractory epilepsy, New England Journal of Medicine, Feb. 2000, pp. 314-319, vol. 342 issue 5.

A.M. Feyissa et al., High-frequency oscillations in awake patients undergoing brain tumor-related epilepsy surgery, Neurology, Mar. 2018, pp. e1119-e1125, vol. 90.

M.S. Berger et al., Brain mapping techniques to maximize resection, safety, and seizure control in children with brain turmors, Neurosurgery, Nov. 1989, pp. 786-792, vol. 25 issue 5.

M.S. Berger et al., Intraoperative brain mapping techniques in neuro-oncology, Stereotactic and Functional Neurosurgery, 1992, pp. 153-161, vol. 58.

C.I. Eseonu et al., Awake Craniotomy vs Craniotomy Under General Anesthesia for Perirolandic Gliomas: Evaluating Perioperative Complications and Extent of Resection, Neurosurgery, Sep. 2017, pp. 481-489, vol. 81 Issue 3.

W.J. Marks et al., Aminoff's Electrodiagnosis in Clinical Neurology (6th Edition), L. Saunders Ed., Chapter 7—Invasive Clinical Neurophysiology in Epilepsy and Movement Disorders, 2012.

E. Formaggio et al., Frequency and time-frequency analysis of intraoperative ECoG during awake brain stimulation, Frontiers in Neuroengineering, 2013, vol. 6.

J.M. Voorhies et al., Techniques for placement of grid and strip electrodes for intracranial epilepsy surgery monitoring: Pearls and pitfalls, Surgerical Neurology International, 2013, vol. 4.

A.R. Wyler et al., Subdural strip electrodes for localizing epileptogenic foci, Journal of Neurosurgery, 1984, pp. 1195-1200, vol. 60.

Davis, New Fibre Optic Sensor for Respiratory Monitoring, Engineering Information Abstracts (Part II), p. 122-123.

Bashirullah, Wireless Implants, IEEE Microwave Magazine, Dec. 2010, pp. S14-S23, vol. 11, issue No. 7.

Chen, A. et al., "Wireless Wearable Ultrasound Sensor on a Paper Substrate to Characterize Respiratory Behavior", ACS Sensors, Mar. 2019, vol. 4, No. 4, pp. 944-952 <DOI:10.1021/acssensors.9b00043>.

Cop, W., "Methods and Devices Used in Ventilatory Monitoring", Encyclopedia of Medical Devices and Instrumentation, 1988, vol. 4, pp. 2870-2877.

Guder, F. et al., "Paper-Based Electrical Respiration Sensor", Angewandte Chemie International Edition, May 2016 [available online Apr. 2016], vol. 55, No. 19, pp. 5727-5732 <DOI:10.1002/anie.201511805>.

Guin, P. et al., "Design of efficient loadcell for measurement of mechanical impact by piezoelectric PVDF film sensor", AIP Advances, Sep. 2016, vol. 6, No. 9, article No. 095122, 5 pages <DOI:10.1063/14964148>.

Harris. G. et al., "The impact of piezoelectric PVDF on medical ultrasound exposure measurements, standards, and regulations", IEEE transactions on ultrasonics, ferroelectrics, and frequency control, Nov. 2000, vol. 47, No. 6, pp. 1321-1335 <DOI:10.1109/58.883521>.

Jow et al., Design and Optimization of Printed Spiral Coils for Efficient Transcutaneous Inductive Power Transmission, IEEE Transactions on Biomedical Circuits and Systems, Sep. 2007, pp. 193-202, vol. 1, Issue No. 3.

Miagori, V. et al., "Ultrasonic sensors in air", Ultrasonics Symposium (Oct. 31-Nov. 3, 1994), 1994, vol. 1, pp. 471-481.

O'Reilly, M. et al., "A PVDF receiver for ultrasound monitoring of transcranial focused ultrasound therapy", IEEE Transactions on Biomedical Engineering, Sep. 2010 [IEEE date of publication: May 2010], vol. 57, No. 9, pp. 2286-2294 <DOI: 10.1109/TBME.2010.2050483>.

Raboel et al., Intracranial Pressure Monitoring: Invasive versus Non-Invasive Methods—a Review, Critical Care Research and Practice; vol. 2012 Article ID 950393, Accepted Mar. 27, 2012.

Ramrakhyani et al., Design and Optimization of Resonance-Based Efficient Wireless Power Delivery Systems for Biomedical Implants, IEEE Transactions on Biomedical Circuits and Systems, Feb. 2011 [IEEE publication date: Oct. 2010], pp. 48-63, vol. 5, issue No. 1.

(56) References Cited

OTHER PUBLICATIONS

Ramrakhyani et al., On the Design of Efficient Multi-Coil Telemetry System for Biomedical Implants, IEEE Transactions on Biomedical Circuits and Systems, Feb. 2013 [IEEE publication date Apr. 2012], pp. 11-23, vol. 7, issue No. 1.
Seo, M. et al., "A simple breathing rate-sensing method exploiting a temporarily condensed water layer formed on an oxidized surface", Applied Physics Letters, Feb. 2015, vol. 106, No. 5, article No. 053701, 4 pages <DOI:10.1063/1.4906815>.
Wansch, Small antennas for wireless micro-systems, Active and Passive Electronic Components, 2002, pp. 71-82, vol. 25.
Yu, Y. et al., "Wrinkled nitrile rubber films for stretchable and ultra-sensitive respiration sensors", Extreme Mechanics Letters, Feb. 2017 [available online Dec. 2016], vol. 11, pp. 128-136 <DOI:10.1016/j.eml.2016.12.003>.
Zhang, X., et al., A wireless and passive wafer cleanliness monitoring unit via electromagnetic coupling for semicondutcor/MEMS manufacturing facilities, Sensors and Actuators A: Physical, Nov. 2011, pp. 414-420, vol. 171, issue No. 2.
Abbaspour-Tamijani et al., "A miniature fully-passive microwave back-scattering device for short-range telemetry of neural potentials", 30th Annual International Conference of the IEEE Engineering in Medicine and Biology Society (Vancouver, British Columbia, Canada, Aug. 20-24, 2008), pp. 129-132 <DOI:10.1109/IEMBS. 2008.4649107>.
Arfin, S. et al., "Wireless Neural Stimulation in Freely Behaving Small Animals", Journal of Neurophysiology, Jul. 2009 [available online Apr. 2009], vol. 102, No. 1, pp. 598-605 <DOI:10.1152/jn. 00017.2009>.
Auricchio, First-in-man implantation of leadless ultrasound-based cardiac stimulation pacing system: novel endocardial left ventricular resynchronization therapy in heart failure patients, Europace, p. 1191-1197, 2013.
Auricchio, "Feasibility, safety, and short-term outcome of leadless ultrasound-based endocardial left ventricular resynchronization in heart failure patients: results of the Wireless Stimulation Endocardially for CRT (WiSE-CRT) study," Europace, p. 681-688, 2014.
Bers, D., "Calcium Fluxes Involved in Control of Cardiac Myocyte Contraction", Circulation Research, Aug. 2000, vol. 87, pp. 275-281 <DOI:10.1161/01.RES.87.4275>.
Chen, A. et al., "Low-voltage shock mitigated micro-electromechanical systems structure", Applied Physics Letters, May 2017, vol. 110, No. 20, pp. 201903-1-5 <DOI:10.1063/14983645>.
Chow, E. et al., "Implantable RF Medical Devices: the Benefits of High-Speed Communication and Much Greater Communication Distances in Biomedical Applications", IEEE Microwave Magazine, Jun. 2013, vol. 14, No. 4, pp. 64-73 <DOI:10.1109/MMM. 2013.2248586>.
Davis et al., A new sensor for monitoring chest wall motion during high-frequency oscillatory ventilation, Medical Engineering and Physics, 1999, pp. 619-623, vol. 21.
De Cock, C.C., Comparison of the haemodynamic effects of right ventricular outflow-tract pacing with right ventricular apex pacing, Europace, p. 275-278, Jul. 2003.
De Venuto, D. et al., "RFID transceiver for wireless powering brain implanted microelectrodes and backscattered neural data collection", Microelectronics Journal, Dec. 2014 [available online Sep. 2014], vol. 45, No. 12, pp. 1585-1594 <DOI:10.1016/J.MEJO.2014. 08.007>.
Folke et al., Critical review of non-invasive respiratory monitoring in medical care, Medical and Biological Engineering and Computing, 2003, pp. 377-383, vol. 41.
Franks et al., Contactless respiration monitoring of infants, Medical and Biological Engineering, May 1976, pp. 306-312.
Fregni, F. et al., "A sham-controlled, phase II trial of transcranial direct current stimulation for the treatment of central pain in traumatic spinal cord injury", Pain, May 2006 [available online Mar. 2006], vol. 122, No. 1, pp. 197-209 <DOI:10.1016/j.pain.2006.02. 023>.

Graham, Emmelyn M., Quantitative mapping of aqueous microfluidic temperature with sub-degree resolution using fluorescence lifetime imaging microscopy, Lab on a Chip, p. 1267-1273, 2010.
Guy, Arthur W., Analyses of Electromagnetic Fields Induced in Biological Tissues by Thermographic Studies on Equivalent Phantom Models, IEEE Transactions on Microwave Theory and Techniques, p. 205-214, Feb. 1971.
Harrison, R., "Designing Efficient Inductive Power Links for Implantable Devices", 2007 IEEE International Symposium on Circuits and Systems (New Orleans, Louisiana, Jun. 2007), pp. 2080-2083 <DOI: 10.1109/SCAS.2007 .378508>.
Hirt, M. et al., "Functional improvement and maturation of rat and human engineered heart tissue by chronic electrical stimulation", Journal of Molecular and Cellular Cardiology, Sep. 2014 [available online May 2014], vol. 74, pp. 151-161 <DOI:10.1016/j.yjmcc. 2014.05.009>.
Hossmann, K.A., Effects of Electromagnetic Radiation of Mobile Phones on the Central Nervous System, Bioelectromagnetics, p. 49-62, 2003.
Ito, Development and Characteristics of a Biological Tissue-Equivalent Phantom for Microwaves, Electronics and Communications in Japan, p. 67-77, 2001.
Kampianakis, E. et al., "A dual-band wireless power transfer and backscatter communication approach for implantable neuroprosthetic devices", 2017 IEEE International Conference on RFID (Phoenix, Arizona, May 9-11, 2017), Jun. 2017, pp. 67-72 <DOI:10.1109/ RFID.2017.7945589>.
Knops, Chronic Performance of a Leadless Cardiac Pacemaker, Journal of the American College of Cardiology, p. 1497-1504, Apr. 21, 2015.
Larson, P. et al., "Miniature ultrasonically powered wireless nerve cuff stimulator", 2011 5th International IEEE/EMBS Conference on Neural Engineering (Cancun, Mexico, Apr. 27-May 1, 2011), pp. 265-268 <DOI:10.1109/NER.2011.5910538>.
Leclercq, C., Comparative effects of permanent biventricular and right-univentricular pacing in heart failure patients with chronic atrial fibrillation, European Heart Journal, p. 1780-1787, Nov. 2002.
Lee, E. et al., "A Biomedical Implantable FES Battery-Powered Micro-Stimulator", IEEE Transactions on Circuits and Systems-I: Regular Papers, Oct. 2009 [IEEE Date of Publication: Dec. 2009], vol. 56, No. 12, pp. 2583-2596 <DOI:10.1109/TCSI.2009. 2034052>.
Lee, S. et al., "A Low-Power Bidirectional Telemetry Device With a Near-Field Charging Feature for a Cardiac Microstimulator", IEEE Transactions on Biomedical Circuits and Systems, Apr. 2011 [IEEE Date of Publication: Aug. 2011], vol. 5, No. 4, pp. 357-367 <DOI:10.1109/TBCAS.2011.2126570>.
Lee, H. et al., "A Power-Efficient Wireless System With Adaptive Supply Control for Deep Brain Stimulation", IEEE Journal of Solid-State Circuits, Sep. 2013, vol. 48, No. 9, pp. 2203-2216 <DOI:10.1109/JSSC.2013.2266862>.
Liu, Shiyi, Wireless Passive Stimulation of Engineered Cardiac Tissues, ACS Sensors, p. 1006-12, 2017.
McDermott, H., "An advanced multiple channel cochlear implant", IEEE Transactions on Bio-medical Engineering, Jul. 1989, vol. 36, No. 7, pp. 789-797 <DOI:10.1109/10.32112>.
Means, David L., Evaluating Compliance with FCC Guidelines for Human Exposure to Radiofrequency Electromagnetic Fields, FCC Office of Technology Bulletin 65, Supplement C, p. 1-53, Jun. 2001.
Migrino, Raymond Q., Assessment of Segmental Myocardial Viability Using Regional 2-dimensional Strain Echocardiography, Journal of the American Society of Echocardiography, p. 342-351, Apr. 2007.
Miller et al., Standardisation of sprirometry, European Respiratory Journal, 2005, pp. 319-338, vol. 26 No. 2.
Nakajima et al., Monitoring of heart and respiratory rates by photoplethysmography using a digital filtering technique, Medical Engineering and Physics, 1996, pp. 365-372, vol. 18 No. 5.
Navaei, Ali, Electrically conductive hydrogel-based microtopographies for the development of organized cardiac issues, Royal Society of Chemistry Advances, p. 3302-3312, 2017.

(56) References Cited

OTHER PUBLICATIONS

Navaei, Ali, Gold nanorod-incorporated gelatin-based conductive hydrogels for engineering cardiac tissue constructs, Acta Biomaterialia, p. 133-146, May 2016.

Navaei, A. et al., "PNIPAAm-based biohybrid injectable hydrogel for cardiac tissue engineering", Acta Biomaterialia, Mar. 2016 [available online Dec. 2015], vol. 32, pp. 10-23 <DOI:10.1016/j.actbio.2015.12.019>.

Nilsson et al., Monitoring of Respiratory Rate in Postoperative Care Using a New Photoplethysmographic technique, Journal of Clinical Monitoring and Computing, 2000, pp. 309-315, vol. 16 No. 4.

Niosh Spirometry Training Guide, Dec. 1, 2003, pp. 1-257, Universities Occupational Safety and Health Educational Resource Center and Centers for Disease Control and Prevention National Institute for Occupational Safety and Health.

Obeid, D. et al., "Low power microwave systems for heartbeat rate detection at 2.4, 5.8, 10 and 16 GHz", 2008 First International Symposium on Applied Sciences on Biomedical and Communication Technologies {Aalborg, Denmark, Oct. 25-28, 2008; pp. 1-5 <DOI:10.1109/ISABEL.2008.4712623>.

Okano, Yoshinobu, The SAR Evaluation Method by a Combination of Thermographic Experiments and Biological Tissue-Equivalent Phantoms, IEEE Transactions on Microwave Theory and Techniques, p. 2094-2103, Nov. 2000.

Ovadia, Marc, The Electrode-Tissue Interface in Living Heart: Equivalent Circuit as a Function of Surface Area, Electroanalysis, p. 262-272, 1998.

Peckham, P. et al., "Functional Electrical Stimulation for Neuromuscular Applications", Annual Review of Biomedical Engineering, Aug. 2005 [available online Mar. 2005], vol. 7, pp. 327-360 <DOI:10.1146/annurev.bioeng.6.040803.140103>.

Pfurtscheller, G. et al., "'Thought'-control of functional electrical stimulation to restore hand grasp in a patient with tetraplegia", Neuroscience Letters, Nov. 2003, vol. 351, pp. 33-36 <DOI:10.1016/s0304-3940{03)00947-9>.

Piezo Film Sensors Technical Manual, Apr. 1999, pp. 1-89, Measurement Specialties, Inc.

Prinzen, Frits W., Relation Between the Pacing Induced Sequence of Activation and Left Ventricular Pump Function in Animals, Journal of Pacing and Clinical Electrophysiology, p. 484-98, Apr. 2002.

Radioactive Consumer Products, Glossy Paper, www.orau.org/PTP/collection/consumer"/o20products/magazines.htm <http://www.orau.org/PTP/collection/consumer%22/o20products/magazines.htm>, 2009, pp. 1-2.

Reddy, Vivek, Cardiac Resynchronization Therapy with Wireless Left Ventricular Endocardial Pacing, Journal of the American College of Cardiology, p. 2119-2129, May 2, 2017.

Ren, H. et al., "Improved current and power density with a microscale microbial fuel cell due to a small characteristic length", Biosensors and Bioelectronics, Nov. 2014 [available online Jun. 2014], vol. 61, pp. 587-592 <DOI:10.1016/j.bios.2014.05.037>.

Schulman, J., "The Feasible FES System: Battery Powered BION Stimulator", Proceedings of the IEEE, Jul. 2008, vol. 96, No. 7, pp. 1226-1239 <DOI:10.1109/JPROC.2008.922588>.

Schwan, H. et al., "The Conductivity of Living Tissues", Annals of the New York Academy of Sciences, Aug. 1957, vol. 65, No. 6, pp. 1007-1013 <DOI:10.1111/j.1749-632.1957.tb36701.x>.

Schwerdt, Helen N., Analysis of Electromagnetic Fields Induced in Operation of a Wireless Fully Passive Backscattering Neurorecording Microsystem in Emulated Human Head Tissue, IEEE Transactions on Microwave Theory and Techniques, p. 2170-2176, May 2013.

Schwerdt, Helen N., A fully Passive Wireless Backscattering Neurorecording Microsystem Embedded in Dispersive Human-Head Phantom Medium, IEEE Electron Device Letters, p. 908-910, Jun. 2012.

Schwerdt, Helen N., A Fully Passive Wireless Microsystem for Recording of Neuropotentials Using RF Backscattering Methods, Journal of Microelectromechanical Systems, p. 1119-1130, Oct. 2011.

Schwerdt, H. et al., "Preliminary thermal characterization of a fully-passive wireless backscattering neuro-recording microsystem", 2011 16th International Solid-State Sensors, IEEE Actuators and Microsystems Conference {Beijing, China, Jun. 5-9, 2011), [Date Added to IEEE Xplore: Aug. 2011], pp. 1228-1231 <DOI:10.1109/TRANSDUCERS.2011.5969400>.

Se Dong Min et al., A study on a non-contacting respiration signal monitoring system using Doppler ultrasound, medical and Biological Engineering and Computing, Nov. 2007, pp. 1113-1119, vol. 45 issue 11.

Seif-Naraghi, Sonya B., Safety and Efficacy of an Injectable Extracellular Matrix Hydrogel for Treating Myocardial Infarction, Science Translational Medicine, p. 1-10, Feb. 20, 2013.

Semmes et al., Subjective and Objective Measurement of Tidal Volume in Critically Ill Patients, Chest Journal, May 1985, pp. 577-579, vol. 87 issue 5, Official Publication of the American College of Chest Physicians.

Shimada, Y. et al., "Clinical use of percutaneous intramuscular electrodes for functional electrical stimulation", Archives of Physical Medicine and Rehabilitation, Oct. 1996, vol. 77, No. 10, pp. 1014-1018 <DOI:10.1016/s0003-9993(96)90061-1 >.

Siew-Mooi Ching et al., Detection of airflow limitation using a handheld spirometer in a primary care selling, Respirology, Apr. 7, 2014, pp. 689-693, vol. 19.

Simmons, Inside Laser Printer Toner: Wax, Static, Lois of Plastic, Mar. 23, 2015, www.wired.com/2015/03/hals-inside-printer-toner/.

Smith, B. et al., "An Externally Powered, Multichannel, Implantable Stimulator for Versatile Control of Paralyzed Muscle", IEEE Transactions on Bio-medical Engineering, Jul. 1987, vol. BME-34, No. 7, pp. 499-508 <DOI:10.1109/tbme.1987 .325979>.

Sun, Y. et al., Wirelessly powered implantable pacemaker with on-chip antenna, 2017 IEEE MTT-S International Microwave Symposium {Honolulu, Hawaii, Jun. 4-9, 2017), [IEEE Date of Publication: Oct. 2017], pp. 1242-1244 <Doi:10.1109/MWSYM.2017.8058831 >.

Sweeney, Michael 0., A New Paradigm for Physiologic Ventricular Pacing, Journal of the American College of Cardiology, p. 282-288, Jan. 17, 2006.

Takahashi, A. et al., "Measurement of intracellular calcium", Physiological Reviews, Oct. 1999 [available online Jan. 1999], vol. 79, No. 4, pp. 1089-1125 <DOI:10.1152/physrev.1999.79.4.1089>.

Tandon, N. et al., "Electrical stimulation systems for cardiac tissue engineering", Nature Protocols, Jan. 2009, vol. 4, No. 2, pp. 155-173 <DOI:10.1038/nprot.2008.183>.

Tandon, N. et al., "Optimization of electrical stimulation parameters for cardiac tissue engineering", Journal of Tissue Engineering and Regenerative Medicine, Jun. 2011 [available online Jan. 2011], vol. 5, No. 6, pp. e115-e125 <DOI:10.1002/term.377>.

Wade, Movements of the Thoracic Cage and Diaphragm in Respiration, The Journal of Physiology, May 28, 1952, pp. 183-212, vol. 124 No. 2.

Walter, P. et al., "Cortical activation via an implanted wireless retinal prosthesis", Investigate Ophthalmology and Visual Science, May 2005, vol. 46, No. 5, pp. 1780-1785 <DOI:10.1167/ovs.04-0924>.

Wang, Jianqing, FDTD calculation of whole-body average SAR in adult and child models for frequencies from 30MHz to 3 GHz, Physics in Medicine and Biology, p. 4119-4127, 2006.

Want, R., "An introduction to RFID technology", IEEE Pervasive Computing, Jan. 2006, vol. 5, No. 1,pp. 25-33 <DOI:10.1109/MPRV.2006.2>.

Wehrle et al., A fibre optic Bragg grating strain sensor for monitoring ventilatory movements, Measurement Science and Technology, 2001, pp. 805-809, vol. 12 No. 7.

Wolf, P., "Thermal Considerations for the Design of an Implanted Cortical Brain-Machine Interface", In: Reichert, W. M. {Ed.), "Indwelling Neural Implants: Strategies for Contending with the In Vivo Environment", CRC Press/Taylor & Francis, 2008, Chapter 3.

(56) References Cited

OTHER PUBLICATIONS

Yamamoto, J. et al., "Low-frequency Electric Cortical Stimulation Has an Inhibitory Effect on Epileptic Focus in Mesial Temporal Lobe Epilepsy", Epilepsia, May 2002, vol. 43, No. 5, pp. 491-495 <DOI:10.1046/.1528-1157.2002.29001.x>.

Yu, Yinghong, Biventricular mechanical asynchrony predicts hemodynamic effect of uni- and biventricular pacing, AJP Heart Circ Physiol, p. H2788-2796, Dec. 2003.

Zealear, D. et al., "The biocompatibility, integrity, and positional stability of an injectable microstimulator for reanimation of the paralyzed larynx", IEEE Transactions on Bio-medical Engineering, Aug. 2001, vol. 48, No. 8, pp. 890-897 <DOI:10.1109/10.936365>.

Zehendner, Christoph, A Simple and Novel Method to Monitor Breathing and Heart Rate in Awake and Urethane-Anesthetized Newborn Rodents, PLOS One, p. 1-9, May 2013.

Zhang, X. et al., "Working Distance Comparison of Inductive and Electromagnetic Couplings for Wireless and Passive Underwater Monitoring System of Rinsing Process in Semiconductor Facilities", IEEE Sensors Journal, May 2011 [IEEE Date of Publication: Nov. 2011], vol. 11, No. 11, pp. 2932-2939 <DOI:10.1109/JSEN.2011.2151185>.

Ziaie, B. et al., "A single-channel implantable microstimulator for functional neuromuscular stimulation", IEEE Transactions on Bio-medical Engineering, Oct. 1997, vol. 44, No. 10, pp. 909-920 <DOI:10.1109/10.634643>.

\* cited by examiner

CONTOUR ELECTROCORTICOGRAPHY (ECOG) ARRAY

CROSS-REFERENCE TO RELATED APPLICATIONS

This application claims priority to U.S. provisional application 62/819,042, which was filed on Mar. 15, 2019 and is entitled Contour Electrocorticography (ECoG) Array. The '042 application is incorporated, in its entirety, by reference into this application.

GOVERNMENT LICENSE RIGHTS

This invention was made with government support under 1734806 awarded by the National Science Foundation. The government has certain rights in the invention.

TECHNICAL FIELD

This application relates to systems, devices, and methods involving monitoring brain activity or responses. More specifically, systems, devices, and methods, employing active electrodes or other sensors positioned adjacent to brain matter in order to discern neural signals of the cerebral cortex or other neural sources, are provided herein.

TECHNICAL BACKGROUND

ElectroCorticoGraphy (ECoG) is a neurophysiological technique that allows direct intraoperative cortical electrical activity recording from the cerebral cortex. This technique was developed by Penfield and Jasper in the 1940s. ECoG has been used to help define the epileptogenic cortical region intraoperatively and provide surgeons with the same type of the cerebral potential recording as the ElectroEncephaloGram (EEG), but without the scalp and skin interference of an EEG. Intraoperative localization of electrical neuronal patterns using ECoG may assist with intervention techniques in patients with epilepsy, and brain tumor-related epilepsy.

BRIEF DESCRIPTION OF THE DRAWINGS

The accompanying drawings illustrate embodiments and serve to explain principles of operation of possible embodiments, whether or not explicitly provided herein.

DETAILED DESCRIPTION

Figure 1:
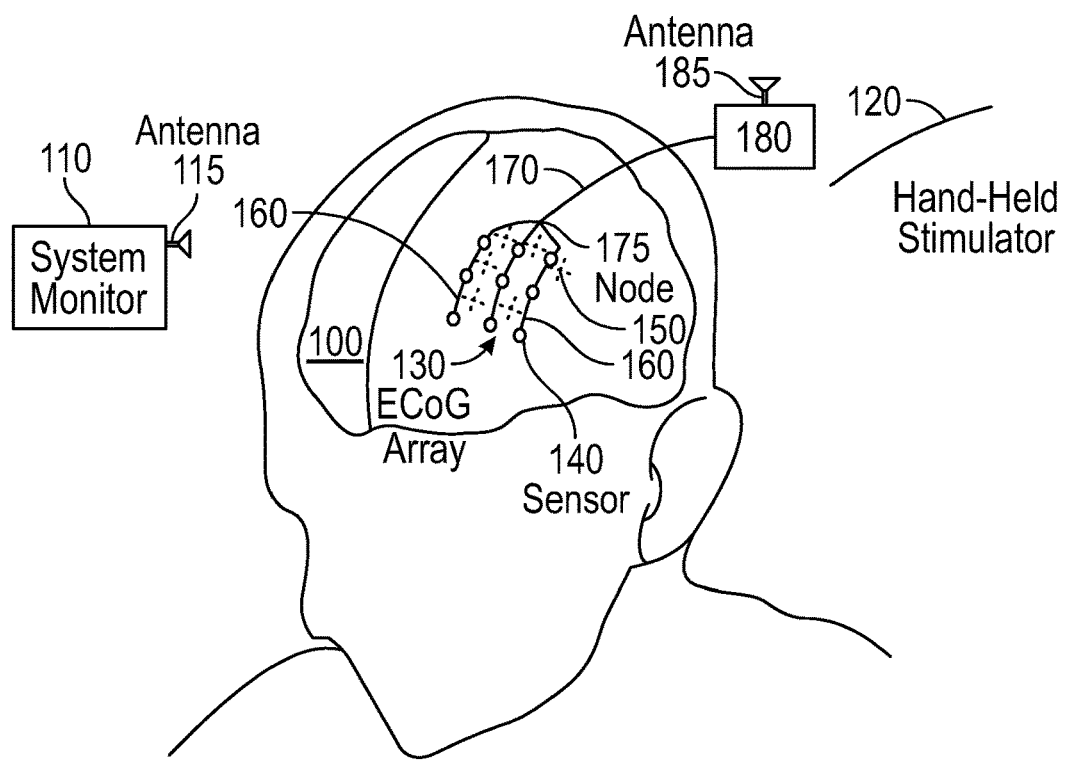
FIG. 1 shows a perspective front view of a human brain with a trident ECoG array and wireless transceiver as may be employed in some embodiments.

Embodiments may include devices, systems, and methods comprising adaptable substrates and sensors with circuit topology or other configurations or designs for performing ECoG testing of a patient. The testing may be performed alone or concurrently with various medical procedures. These substrates may support sensors positioned as an array, and may be employed while accessing specific portions of the cortex or other brain surface by an external stimulator. In embodiments, the sensors may serve to collect neural signals, may stimulate neural signals, and may do both. In embodiments, a suitable number of active electrodes or other sensors positioned as an array may be employed and may serve to provide contour coverage of the brain surface being tested. In some embodiments, wireless transceivers or transmitters may be employed to broadcast the sensed neural signals or information derived using the sensed neural signals to a remote system monitor that may be configured to report real-time brain surface responses from imposed stimulation. The imposed stimulation may come from a hand held stimulator, a robotically manipulated stimulator, and from electrodes or other sensors on the substrate as well.

Substrates of embodiments may be flexible and may be configured such that electrodes or other sensors supported by the substrate may contour a target testing area of a brain of a patient and may receive and report detectable responsive brain signals during the testing. The substrate and sensors may also be configured to allow a surgeon or other medical professional access close to the substrate and sensors during a procedure. This access may be provided by openings in the substrate, by spacings between adjacent substrates, by spacings in the substrate, and by other configurations as well. The substrates may be contoured as well as flexible in order to closely mimic the contours of the cortex, or other brain area, to be tested using ECoG. Because of the flexibility, contours, and/or locations of the sensors, in embodiments little or no need of further manipulation or added pressure to ensure contact may be needed to obtain viable ECoG signals. Also, a practitioner may have access to portions of the cortex or other brain location nearby the sensors and substrate because of the open configuration of the substrate. This proximal access to the cortex or other brain surface area may allow a surgeon or other practitioner to pinpoint specific sensor areas and specific brain surface areas for ECoG testing. In other words, embodiments may provide a practitioner with discrete access in and around sensors located on the cortex for testing of specific brain tissue. Moreover, embodiments may provide individual addressing of sensors such that a practitioner may receive tailored feedback during ECoG testing identifying specific locations of the brain tissue or specific sensor locations of an array or both. Through this tailored ECoG array of sensors, a practitioner may not need to apply any pressure or large amounts of pressure on the sensor or sensors during procedures. Thus, embodiments can provide a practitioner with access to ECoG tests of brain tissue responses using stimulus locations between sensors supported by a substrate.

As examples, embodiments can provide for an array of electrodes positioned and/or configured to: i) simultaneously record neural signals while providing stimulation on specific portions of the cortex using a user-guided stimulator; ii) stimulate multiple sites concurrently and/or independently using multiple electrodes, iii) acquire neural signals over a large cortex area; and/or iv) acquire neural signals at a setting remote from the neural source using wireless or other communication techniques. Other procedures and processes may also be provided by embodiments.

Embodiments may provide ECoG arrays that allow recording of the cortical and subcortical electrical activity while simultaneously enabling the performance of a surgical resection or other procedure by a surgeon. In these and other embodiments, during an awake or other brain procedure, the sensors may be placed on the cortical surface for recording the electrical activities and the identification of epileptiform patterns. These patterns may occur after direct cortical electrical stimulation and may serve as a surrogate for a forthcoming seizure or micro-seizures.

ECoG arrays of embodiments may have several geometries and sizes, which can vary from single strip (one-dimension array) electrodes (1×4 cm or 1×6 cm) or other sensors with a support substrate, to grid electrodes or other sensors (two-dimensional array) on a substrate. In embodiments, the strip electrode (one-dimensional array) or other sensor may only support monitoring in one direction (e.g., superior) unless multiple strips are placed, and the grid electrodes or other sensors (two-dimensional array) may allow procedures to be performed over a large desired area because of the larger access area these embodiments may provide.

As noted above, embodiments, may include flexible substrate materials that provide appropriate electrode or other sensor contact with the brain. Embodiments may also include transmission systems to allow sensor signals to be transmitted with wires or wirelessly from a testing location to a system monitor for observance or other use during or after a medical procedure. Thus, embodiments may employ a system monitor or another device to record neural signals in-situ during brain surgery. This recording of neural signals may be collected by the system monitor or elsewhere while stimulating specific portions of the cortex using a hand-held stimulator or other stimulator. Embodiments may be configured to perform recording through configurations that allow access within and around the ECoG arrays while recording neural signals.

Embodiments may provide access during a medical procedure by: selectively placed material layers of the substrate, which can provide direct access as well as indirect access; through connection access points in a substrate or between substrates; through wireless communications between sensors and a system monitor or other component; through spaced electrodes in two-dimensional arrays; and through other techniques and system topologies. For example, in some embodiments, one or more perforations or openings on the array substrate may be provided to allow for in-situ recording and simultaneous stimulation by a surgeon or other practitioner.

Embodiments may be configured to be placed at or around the contour of the cortex. In so doing, access to suitable signals and/or more signals from the cortex may be acquired. Embodiments may be configured with a thin elastomer layer as a substrate and robust electrodes supported by the substrate. These electrodes or other sensors may be configured to provide monitoring and/or stimulation of active brain tissue. The electrodes or other sensors may be sized such that their weight is sufficient to hold them nearby or up against the surface of the brain being analyzed. This weight, in combination with the configuration of the substrate, e.g., its thickness, shape, and material flexibility, can serve to have an ECoG array lay in direct or near direct contact with the brain surface during testing. This close proximity can provide for sensing low level brain surface responses to stimulation as well as for reduced signal noise in the responses received by a sensor.

Embodiments may also include wireless communication modules to collect and/or transmit neural signals to an external reader, system manager, or other recipient. Embodiments may comprise wireless perforated ECoG arrays such that specific portions of the cortex may be accessed by an external stimulator while concurrently collecting neural signals by the ECoG array. These and other embodiments may employ sensors of various array sizes and configurations. The array configurations may include one-dimensional arrays as well as two-dimensional and three-dimensional arrays. The number of sensors on each array may be consistent and may differ. In some embodiments individual arrays may be addressable, and in some embodiments individual sensors may be addressable.

In some embodiments a procedure may be performed first using a first array and then a larger or smaller array may be subsequently used. This switch in array size may provide improved contour coverage of the brain surface during a procedure. Likewise, selecting a particular array size for a procedure, may also be tailored for specific contour coverage during the procedure. In other words, a small 1×2 or 1×4 or 2×2 or 3×3 or 2×3, etc. array may be selected for a small area of the cortex to be tested while a larger 12×12 or 10×10 or 15×8, etc. array may be selected for a larger subsequent testing area. These testing areas may have the same center or may overlap or may not overlap at all. Also, different size arrays may be selected in order to obtain adequate coverage during a procedure. In other words, a 3×3 or other smaller array may be used along with, i.e., concurrently with, a larger, e.g., 12×12 or large array, when the area of tissue to be tested may be better mimicked by the differing sizes.

Also, embodiments may employ substrates of different sizes and configurations. These configurations can include different shapes and different arcs of curvature. Both the selected shapes and arcs of curvature may be selected to closely mimic the curvature of the brain surface to be tested. As noted above, the more closely the sensors lay on the tissue the better the received test results may be.

Various features, steps, processes, components, and sub-components, as may be employed in embodiments, are provided above and below. These features, steps, processes, components, subcomponents, partial steps, systems, devices, etc. may be adjusted, combined and modified in various fashions and various ways among and between the teachings and figures provided herein, as well as in other ways not specifically described herein.

Embodiments, therefore, may provide, a tailored design/implementation of ECoG arrays for use by neuro-surgeons or others in some embodiments, this tailored design may be adopted by manufacturers for large scale production while also providing tailored ECoG array features accessible for use by neuro-surgeons or other users. Embodiments may also provide ECoG arrays that allow recording cortical and subcortical electrical activity while simultaneously performing a surgical resection or other procedure.

Embodiments may be configured to be placed at or around the contour of the cortex and may be flexible enough, through the use of flexible and thin materials, to contour or mimic the cortex area beneath the placed sensor. In so doing, access to more suitable signals and/or more signals from the cortex may be acquired. Likewise, individual and/or concurrent electrode stimulus may also be provided. Thus, embodiments may be configured with a thin elastomer substrate layer and robust electrodes, to provide monitoring and/or stimulation of a cortex area.

Still further, as noted above, embodiments may also include wireless communication modules to collect and/or transmit neural signals to an external reader, system monitor, or other recipient. The electrodes, in embodiments, may provide forces serving to hold the thin elastomer layer to the cortex or other source of signals being monitored or stimulated. These forces may be primarily generated by the actual weight/mass of the electrodes or other sensors. In some embodiments, the weight/mass of the electrodes or other sensors may be sized to deflect or deform or otherwise contour the flexible material of a sensor to closely or exactly mimic and be adjacent to or close to the cortex or other neural signal source.

Embodiments may comprise real-time neural electrocorticography (ECoG) measurement systems that may comprise a flexible substrate, the substrate comprising a plurality of tines with each tine comprising a plurality of sensor electrodes. In this and other embodiments, each tine may have an arc of curvature, the arc of curvature having a diameter that serves to define the arc of curvature along a single curve or a complex curve. In embodiments, the arc of curvature may have diameters of 7.5 cm, 9 cm, 12.5 cm. 19 cm, and infinity. Other diameters in this range, as well as smaller dimeters and in different increments, may also be employed in embodiments. The biocompatible material may be a silicone or flexible polyethylene, polypropylene or other flexible polymer. In some embodiments, the substrate may be a silicone substrate. In this and other embodiments, an open spacing, i.e., a gap or void in the substrate, may exist between adjacent tines of the plurality of tines and a wired connector may be connected to an output of the plurality of sensors. Still further, a wireless transceiver may be in communication with the wired connector and each sensor electrode of the plurality of sensor electrodes may have a mass of 3 mg to 98 mg in increments between as small as 0.1 grams or even smaller. Still further, the transceiver may employ circuit topology configured to send neural signals received from the sensor electrodes to a system monitor. In embodiments, the circuit topology of the transceiver may be configured to provide contemporaneous reporting of neural signals received from the sensor electrodes when external stimulation is provided between sensor electrodes of the plurality of sensor electrodes. In embodiments, the system monitor may be configured to receive the contemporaneous neural signals from the transceiver and to record the received contemporaneous neural signals. In embodiments, a substrate may be coated with no more than 0.8 mm of medical grade silicone. In embodiments, a substrate may comprise no more than 0.8 mm of medical grade silicone. In embodiments, a flexible two-dimensional substrate may be in the shape of a trident. In embodiments, the sensors may be equidistantly spaced along tines of the substrate.

Embodiments, may comprise a neural sensor comprising a first one-dimensional array of sensors, wherein at least one sensor in the first array may have a mass of 98 mg and a second one-dimensional array of sensors, wherein at least sensor in the second array may have a mass of 98 mg. A silicone substrate may also be employed to support the first array and the second array, and the silicone substrate may have a thickness of no greater than 0.8 mm. A communication circuit may also be employed. This communication circuit, which may include a local transceiver such as local receiver 180 and antenna 185 of FIG. 1, may be tethered to a node, the node electrically connected to the first array or the second array or both. In embodiments, the sensors of the first array may be circular and may be spaced apart from each other at least by their average circumference. In embodiments, the first array and the second array may be positioned on tines of a triton and the spacing between the first array and the second array may at least be 2.0 mm, other spacings may also be used. In embodiments, the node may be coupled to a transceiver, the transceiver configured to provide contemporaneous reporting of neural signals received from the sensors when external stimulation is provided between sensors of the first one-dimensional array and the second one-dimensional array. In embodiments, the first one-dimensional array and the second one-dimensional array may be parallel to each other. In embodiments, the transceiver may be configured with an antenna and the transceiver may be configured to wirelessly communicate with a system monitor.

Embodiments may include a real-time neural electrocorticography (ECoG) measurement system comprising a flexible two-dimensional substrate, the substrate comprising a plurality of arrays with each array comprising a plurality of sensors. In embodiments, each array may have an arc of curvature that may be at least nineteen centimeters in length; the substrate may comprise a biocompatible material; and an open spacing may exist between adjacent arrays of the plurality of arrays. In embodiments, a wired connector may be connected to an output of the plurality of sensors and a wireless transceiver may be in communication with the wired connector. In embodiments each sensor of the plurality of sensors may have a mass of 3.0 mg to 98 mg and the transceiver may have a circuit topology configured to send neural signals received from the sensors to a system monitor. In embodiments, the arrays may be one-dimensional arrays and the circuit topology of the transceiver may be configured to provide contemporaneous reporting of neural signals received from the sensors when external stimulation is provided between sensors of the plurality of sensors. In embodiments, the system monitor may be configured to receive the contemporaneous neural signals from the transceiver and to record the received contemporaneous neural signals. In embodiments, the substrate may comprise no more than 0.8 mm of medical grade silicone and the flexible two-dimensional substrate may be in the shape of a polygon. In embodiments, the sensors may be equidistantly spaced along one-dimensional arrays of the substrate.

FIG. 1 shows a perspective front view of a human brain with a trident ECoG array as may be employed in some embodiments. The brain 100 is shown with a trident shaped ECoG array 130. Also shown are the system monitor 110 and the hand-held stimulator 120 as well as antennas 185 and 115 and node 175. The node 175 is shown as a connection junction between connections 160, and the connection 170. During a procedure, the handheld stimulator 120 may be placed at various testing points 150 and provide a stimulating voltage to the particular testing point of brain tissue. The sensors 140, which may be electrodes, nearest the testing point 150 being stimulated, may sense brain signals and report these sensed signals back through connections 160 and 170. These connections 160 and 170 may comprise a wire or other electrical pathway supported by a flexible substrate. The flexible substrate may have an inherent curve or bow. Connection 170 may be coupled to a wireless transmitter that may itself be communicating with system monitor 110. The system monitor 110 may take the received data and determine which one or more sensors 140 are receiving response signals from the brain tissue and the magnitude of each received signal at the particular sensor. This received and determined information may then be reported to the practitioner performing the procedure and may also be stored for later analysis. As can be seen in FIG. 1, the connections 160 may be spaced apart from one another and may have multiple sensors laying along their lengths. As can also be seen, the substrate connections 160 may be tines, and may be oriented as tines of a fork, as shown in FIG. 1. The array 130, which is trident shaped, may also have various other shapes in embodiments. These may include connection loops with sensors, one or more spars with one or more sensors, elliptical, circular, triangular, polygonal, and other configurations as well. The connection 170 serves as a common bus for the connections 160 between them and a local receiver 180. This local receiver 180 may be a transceiver communicating back and forth with the system monitor 110. In embodiments, the connection 170 may be hardwired directly with the system monitor 110 and may not have an intervening local receiver. An advantage of the local receiver may be additional access being provided in and around the target tissue testing site because of the absence of a wired lead connection between the array 130 and the system monitor.

The substrate in FIG. 1, which is positioned around the connections 160, as well as in other embodiments, may comprise 0.25 mm-0.7 mm thick medical grade emulated silicone as well as other materials including those with similar properties to silicone. Embodiments may employ silicone between 0.5 mm and 0.7 mm and less than 0.75 mm. Other FDA materials approved for cortex applications may be considered, provided they have a flexure under the weight of the electrodes to contour or mimic the surface arc of the cortex in which will be monitored by the sensor.

Embodiments may be made through various manufacturing techniques including 3D printing, extrusion, and injection molding. The electrodes or other sensors of embodiments may have various thicknesses including 0.125 mm, 0.25 mm. 0.3 mm. 0.4 mm, 0.5 mm, 0.6 mm, 0.7 mm, and 0.8 mm as well as being thinner or thicker in embodiments. Conductive Ag epoxy may be used to connect wires from a sensor array/stimulator array to a 10-pin cable for communication to and from the sensor. Other connection techniques, such as micro-welding, may also be employed to connect the sensor/stimulator to the support circuit. Embodiments may be enclosed by 0.5 mm-thick medical-grade emulated silicone. Thus, arrays, connecting wires, local receivers, etc., may each be coated. This coating material or other coating materials may be selected to allow arrays to easily cover the contour surface of the cortex.

The electrodes or other sensors of embodiments may be circular, cubical, and other shapes. Cylindrical sizes can range from 1.0 mm to 5.0 mm in diameter as well as other sizes. Likewise, polygonal sizes can include these same size ranges. The electrodes or other sensors may be 0.125 mm-thick, which may serve to increase the conformal coverage of electrodes on the contour surface of the cortex or other test location. The electrodes or other sensors may have a mass of 6.80 mg as well as have a range of mass of 3.0 mg-98 mg in increments of 0.1 mg or larger or smaller. In embodiments, the electrodes or other sensors may have enough mass in order to serve to hold the sensor down and to the cortex and to maintain an adjacent or near adjacent juxtaposition between the sensors electrodes and the cortex or other neural system being stimulated and/or monitored. The electrodes or other sensors may also be controlled to provide individual stimulus as well as groupings of stimulus to the cortex or other area being monitored.

Figure 2:
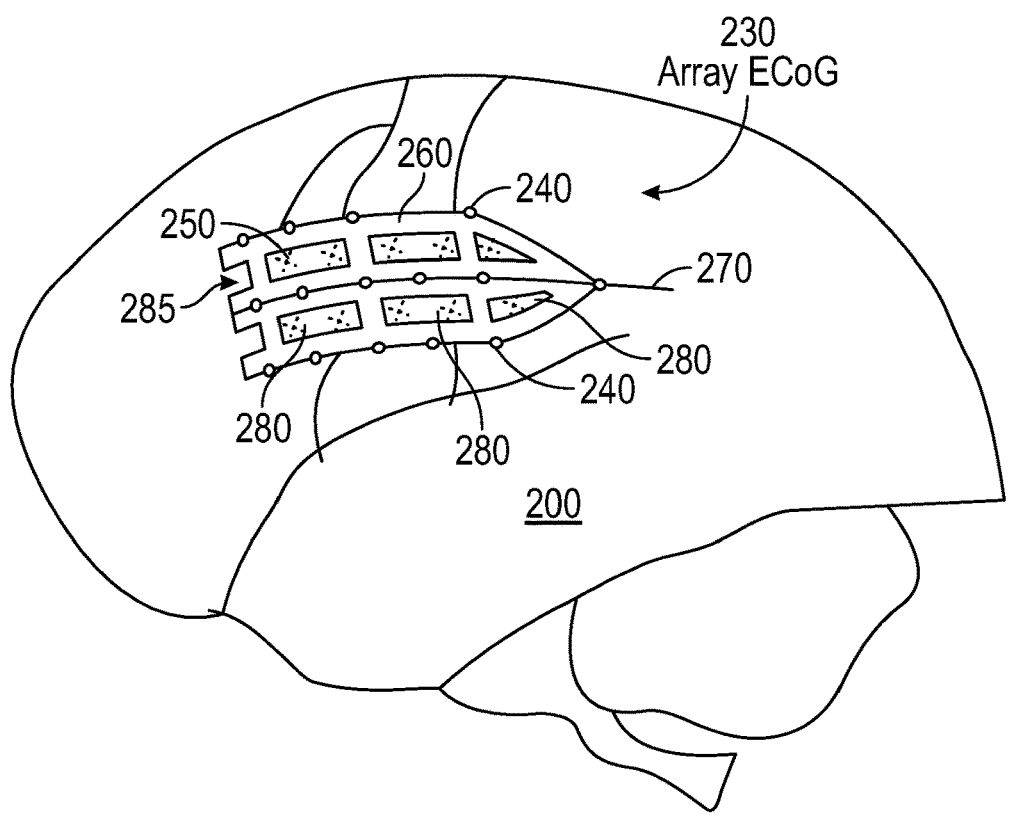
FIG. 2 shows a side view of a brain with an ECoG array as may be employed in some embodiments.

FIG. 2 shows a side view of a brain 200 with an ECoG array 230 as may be employed in some embodiments. The ECoG array 230 in FIG. 2 has multiple sensors 240 along its substrate 260. The substrate 260 in FIG. 2 is shown with openings 280 and end recesses 285. The openings 280 are shown as rectangles but may be circular, oval, and various other shapes. The openings may be sized to allow a practitioner to insert a hand-held stimulator through the opening and onto or near brain tissue to be stimulated and/or otherwise tested or acted upon. Testing points are labelled as 250 in FIG. 2. The sensors 240 may be located along the various edges or other surfaces of the substrate 260 and may be used to receive brain signals responsive to the simulations. These responsive signals may be reported back through the connection 270.

Like the substrate of other embodiments, the substrate in FIG. 2 may be curved and may be flexible such that when placed on or around the brain tissue to be tested, one or more of the sensors 240 of the array 230 come in close proximity or touch the brain tissue to be tested. In some embodiments, a portion of the sensors will touch the brain tissue during testing and in some embodiments all of the sensors of an array will touch the brain tissue during testing. Upon receiving responsive signals, a system monitor may determine which sensors are best positioned relative to the test tissue and may ignore some responsive signals or the absence of responsive signals attributable to poor sensor location.

In embodiments, as in FIG. 2, the substrate may comprise biocompatible materials that are flexible enough to allow the substrate to lie along the contours of the brain area being tested. To further promote the contact between the sensors and the target rain area, the substrate may have simple curves, i.e. curves with one radius of curvature, or complex curves, i.e., curves with two or more radii of curvature, of varying degrees. The radius of curvature may be at least 19 cm in length. The radius of curvature may have diameters of 7.5 cm, 9 cm, 12.5 cm. 19 cm, and infinity. Other diameters in this range, as well as smaller dimeters, may also be employed in embodiments. The increments in the diameter change may be millimeters and centimeters.

During a procedure, multiple arrays of differing sizes and curves may be available for a practitioner and the practitioner may select the appropriate size as well as the appropriate simple or complex curved arrays that best mimic the curvatures of a brain area to be tested or treated during a procedure. FIG. 2 also shows that sensors 240 need not be uniformly spaced across an entire array 230.

Figure 3:
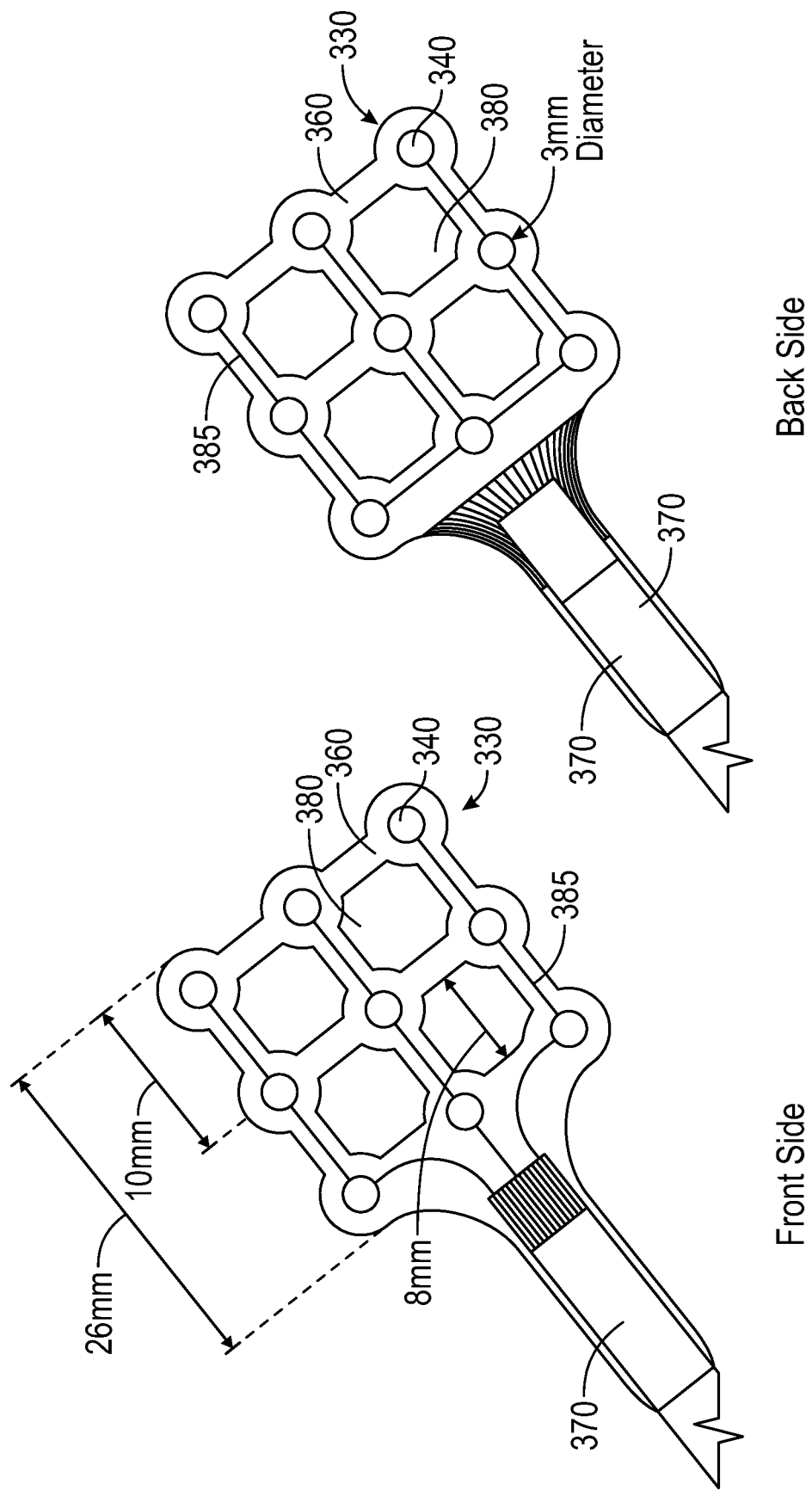
FIG. 3 shows frontside and backside plan views of a 3×3 ECoG array as may be employed in some embodiments.

FIG. 3 shows frontside and backside plan views of a 3×3 ECoG array 330 as may be employed in some embodiments. A ten-pin connector 370 is shown on the backside view. Also labelled in FIG. 3 are the substrate 360 and the sensors 340 along with dimensions of the sensors and the substrate 360. As can be seen, the substrate 360 has a rectangular shape and access openings 380. Electrical pathways are labelled 385 in FIG. 3 and show how sensors may be connected to each other and through the ten-pin connector 370 leaving the array 330. As described elsewhere, this array 330 may also be flexible and may have various contours and curvatures in order to better mimic a target location of the brain. The access openings 380 may be used for stimulator placement during a procedure.

Figure 4:
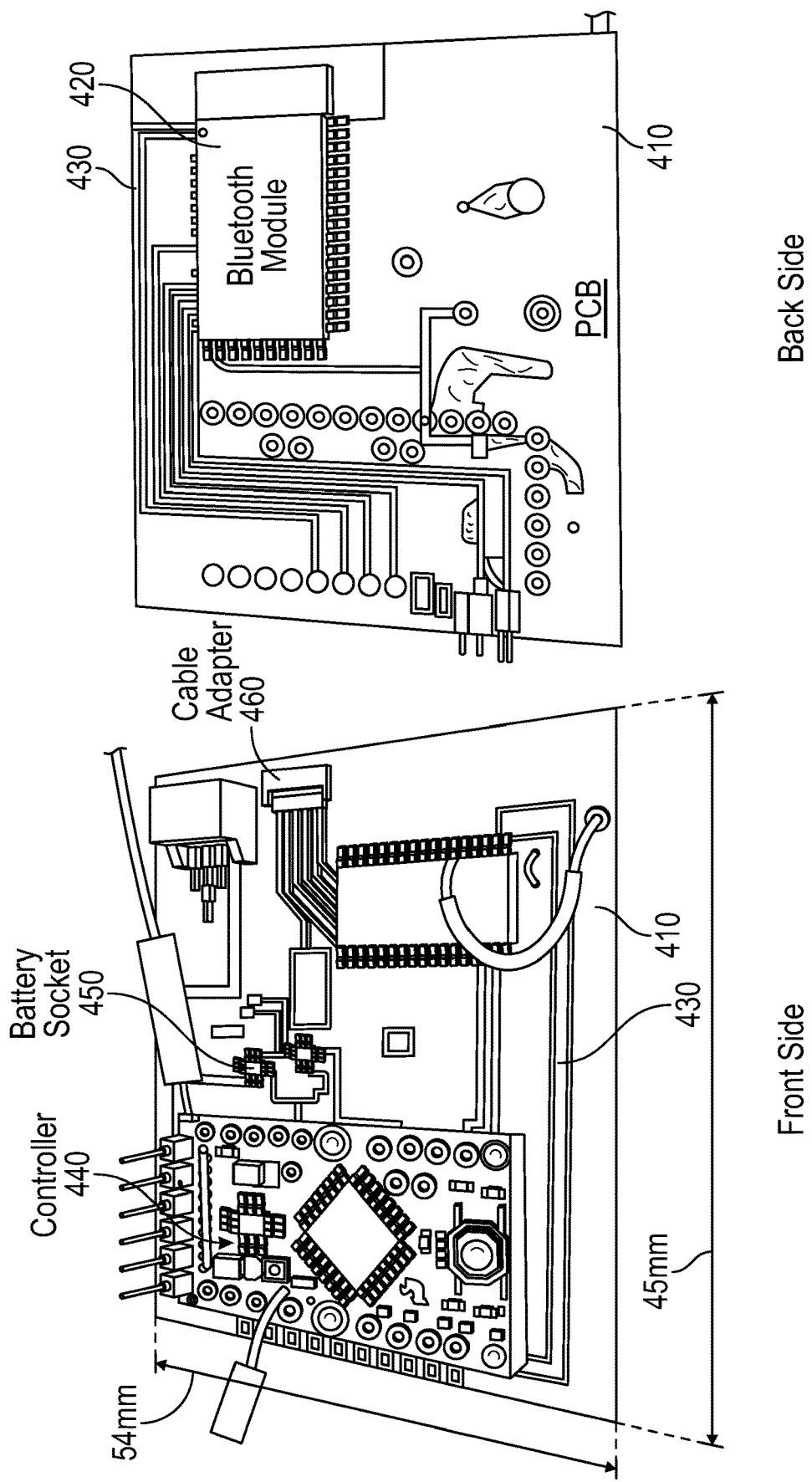
FIG. 4 shows frontside and backside views of electronics that may be employed in ECoG testing devices or systems of some embodiments.

FIG. 4 shows frontside and backside views of electronics mounted to a PCB 410 that may be employed in ECoG testing devices or systems of some embodiments. The frontside view is labeled with controller 440, battery socket 450, cable adapter 460 and multiple electrical pathways 430. The backside view is labelled with printed circuit board 410, wireless communication module 420, and electrical pathways 430. The electronics of FIG. 4 may be connected locally to an array during testing. This connection may be wired and made through the ten-pin cable shown in FIG. 3, as well as through other connection topologies. In embodiments, the connection between the electronics and an array may be detachable so that the electronics may be used with many arrays over time and across multiple procedures. The arrays of embodiments may be sanitized and used a single time or multiple times while the support electronics may be sterilized and reused for many procedures over the lifetime of the electronics. The circuit topology may also include amplifiers, filters, digitizers, batteries, and connecting electronics, as can be seen in FIG. 4. Other electronics may also be employed. As noted, embodiments may employ silicone as an encloser to protect the electronics during sterilization processes. In embodiments, components may be enclosed, except for cable adapter that may receive a 10-pin cable or other connection topology from the ECoG array. Other encapsulation configurations may also be employed.

Figure 5:
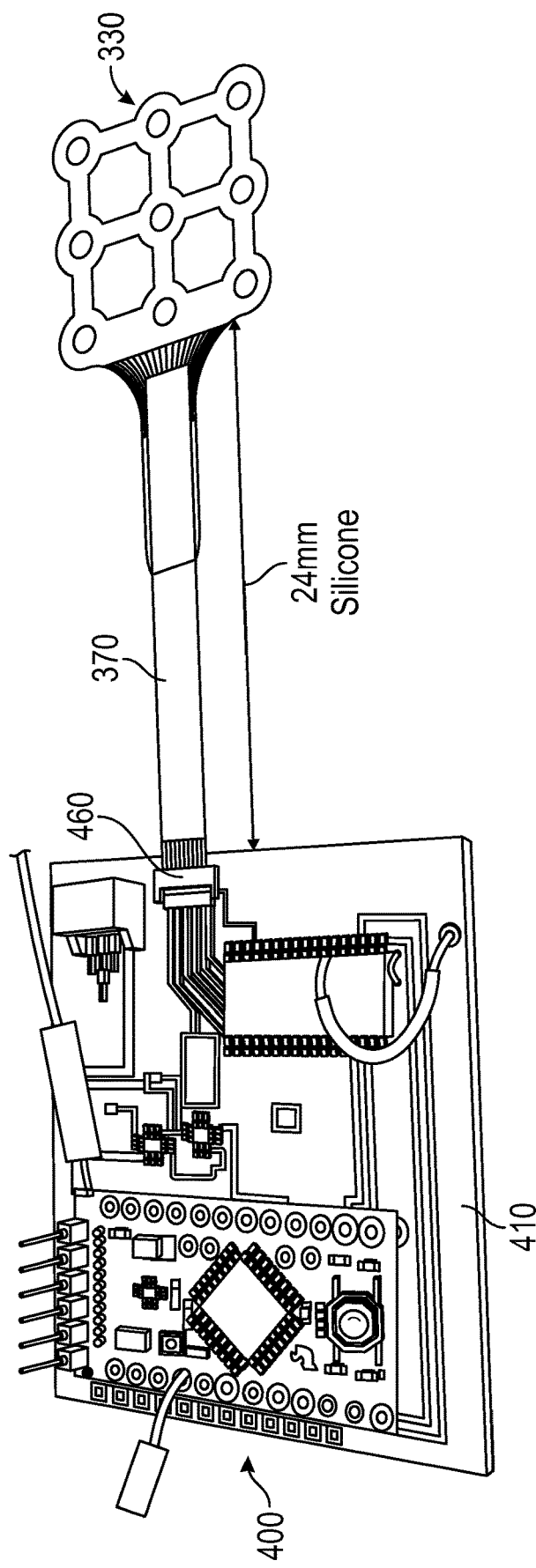
FIG. 5 shows a 3×3 ECoG array connected to a PCB with wireless electronics as may be employed in some embodiments.

FIG. 5 shows a 3×3 ECoG array connected to a PCB with wireless electronics as may be employed in some embodiments. The array 330 is labelled along with the electronics 400 and cable adapter 460 in FIG. 5. As can be seen, the connection 370 may be millimeters in length. Comparatively, in other embodiments, the connection 370 may be tens or hundreds of centimeters in length, or even longer.

The cable adapter 460 may allow for disposable arrays to be used such that new arrays may be used for each procedure while reusing the electronics 400 for many procedures. The silicone overlay 690, which is shown as being 20 mm in length, may also have various lengths and cover some or all of the cabling in embodiments. The silicone overlay may also have various shapes if employed. These shapes can include L configurations. Other connection techniques, designs, and topologies may also be employed in embodiments.

Figure 6:
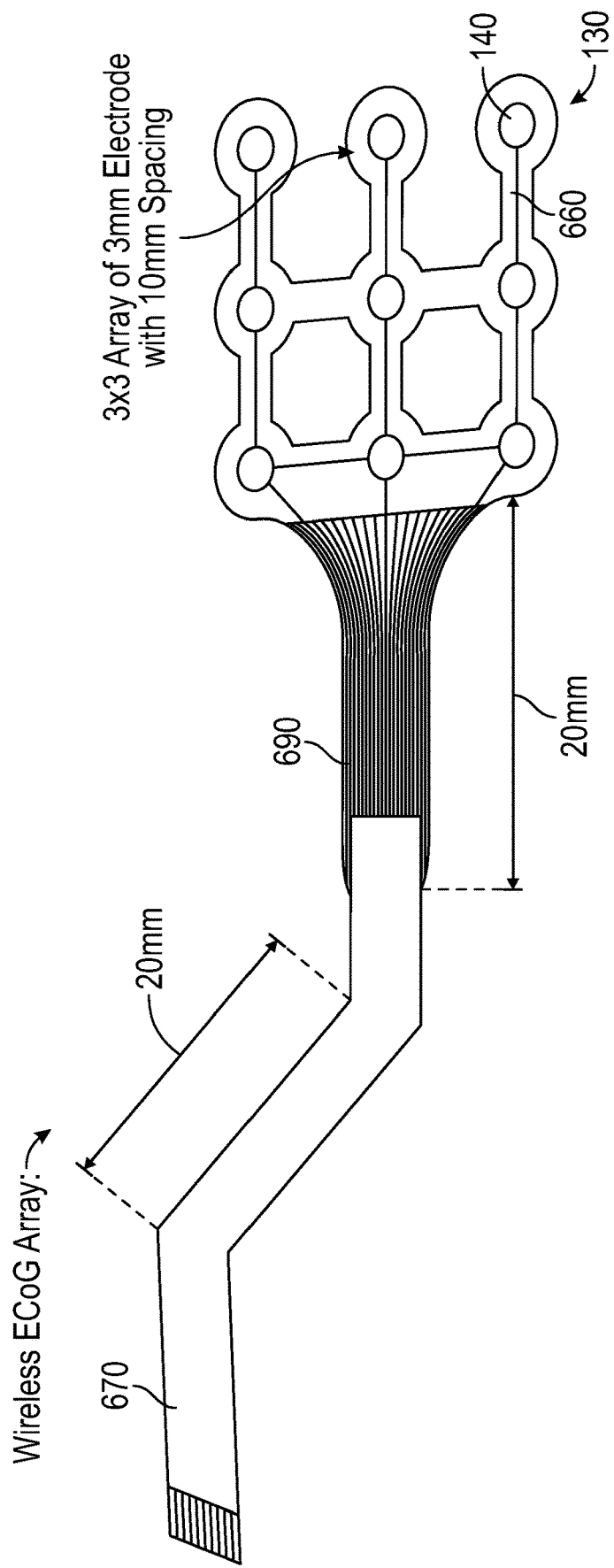
FIG. 6 shows a schematic of a trident ECoG array as may be employed in some embodiments.

FIG. 6 shows a schematic of a trident ECoG array 130 as may be employed in some embodiments. Also labelled in FIG. 6 are substrate tines 660, sensors 140 located along these tines 660, and connection pathway 670. The connection pathway 670 shows an end with a ten-pin connection strip for connection to electronics 400 shown in earlier figures as well as for connection to other electronics in some embodiments. The lengths of the connection pathway 670 are also identified in FIG. 6 and show how the material of the connection pathway 670 may transition from substrate material to an electrical ribbon along the length of the connection pathway 670.

Curved support substrates may be employed by ECoG arrays in some embodiments. The substrates may have various curvatures. These curvatures may lie along a single diameter or be complex curves having two diameters of curvature for a single substrate. While diameters of 7.5 cm, 9 cm, 12.5 cm, 19 cm, and infinity may be used, other diameters in this range, as well as smaller dimeters, may also be employed in embodiments. These diameters of curvature may be applied to simple curves as well as complex curves.

Array calibration may be performed in embodiments. This calibration may serve to correlate stimulus signals with received signals by one or more sensors of an array. This calibration may be performed on a test bench using conductive gel with the array being calibrated. As voltages are applied by a stimulus the responsive signals from the sensors may be monitored and observed. Variations between input (stimulus) and output (sensor) signals may be identified and used to calibrate the electronics and/or system monitor described above. This calibration may include using root-mean square error correction as well as filtering high frequency noise and waveform distortion in the output signal. Through this calibration, output signals of the sensors may be better understood to reflect more accurate traits of the brain tissue being tested.

While embodiments have been illustrated herein, it is not intended to restrict or limit the scope of the appended claims to such detail. In view of the teachings in this application, additional advantages and modifications will be readily apparent to and appreciated by those having ordinary skill in the art. Accordingly, changes may be made to the above embodiments without departing from the scope of invention.

Various features, steps, processes, components, and subcomponents may be employed in certain embodiments. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure unless otherwise indicated herein or otherwise clearly contradicted by context. All methods described herein can be performed in any suitable order unless otherwise indicated herein or otherwise clearly contradicted by context.

The corresponding structures, material, acts, and equivalents of any means or steps plus function elements in the claims are intended to include any structure, material or act for performing the function in combination with other claimed elements. The description of certain embodiments has been presented for purposes of illustration and description, but is not intended to be exhaustive or limited to the form disclosed. Many modifications and variations will be apparent to those of ordinary skill without departing from the scope and spirit of the invention. These embodiments were chosen and described in order to best explain principles of the invention and the practical application, and to enable others of ordinary skill in the art to understand the invention for embodiments with various modifications as are suited to the particular use contemplated.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "about" or "approximately" in reference to a recited numeric value, including for example, whole numbers, fractions, and/or percentages, generally indicates that the recited numeric value encompasses a range of numerical values (e.g., +/−5% to 10% of the recited value) that one of ordinary skill in the art would consider equivalent to the recited value (e.g., performing substantially the same function, acting in substantially the same way, and/or having substantially the same result).

Recitation of ranges of values herein are merely intended to serve as a shorthand method of referring individually to each separate value falling within the range, unless otherwise indicated herein, and each separate value is incorporated into the specification as if it were individually recited herein.

It should be noted that the terms "first", "second", and "third", and the like may be used herein to modify elements performing similar and/or analogous functions. These modifiers do not imply a spatial, sequential, or hierarchical order to the modified elements unless specifically stated.

What is claimed is:

1. A real-time neural electrocorticography (ECoG) measurement system comprising:
    a flexible two-dimensional substrate, the substrate comprising a plurality of tines with each tine comprising a plurality of sensors,
    wherein each tine has an arc of curvature, the arc of curvature being at least nineteen centimeters in length,
    wherein the substrate comprises a biocompatible material,
    wherein a plurality of open spacings exist between adjacent tines of the plurality of tines;
    a wired connector connected to an output of the plurality of sensors; and
    a wireless transceiver in communication with the wired connector,
    wherein each sensor of the plurality of sensors has a mass of 3.0 mg to 98 mg, and
    wherein the transceiver has circuit topology configured to send neural signals received from the sensors to a system monitor.

2. The system of claim 1 wherein circuit topology of the transceiver is configured to provide contemporaneous reporting of neural signals received from the sensors when external stimulation is provided between sensors of the plurality of sensors.

3. The system of claim 1 wherein the system monitor is configured to receive the contemporaneous neural signals from the transceiver and to record the received contemporaneous neural signals.

4. The system of claim 1 further comprising a coating of medical grade silicone with a thickness of no more than 0.8 mm.

5. The system of claim 1 wherein the substrate comprises no more than 0.8 mm of medical grade silicone.

6. The system of claim 1 wherein the flexible two-dimensional substrate is in the shape of a trident.

7. The system of claim 1 wherein the sensors are equidistantly spaced along tines of the substrate.

8. The system of claim 1 wherein the plurality of open spacings further comprises end recesses between the adjacent tines of the plurality of tines.

9. The system of claim 1 wherein at least one cross-member connects the adjacent tines of the plurality of tines.

10. A real-time neural electrocorticography (ECoG) measurement system comprising:
    a flexible two-dimensional substrate, the substrate comprising a plurality of arrays with each array comprising a plurality of electrodes,
    wherein each array has a radius of curvature, the radius of curvature being at least nineteen centimeters in length,
    wherein the substrate comprises a biocompatible material,
    wherein a plurality of open spacings exist between adjacent arrays of the plurality of arrays;
    a wired connector connected to an output of the plurality of electrodes; and
    a wireless transceiver in communication with the wired connector,
    wherein each electrode of the plurality of electrodes has a mass of 3.0 mg to 98 mg, and
    wherein the transceiver has circuit topology configured to send neural signals received from the electrodes to a system monitor.

11. The system of claim 10 wherein the arrays are one-dimensional arrays.

12. The system of claim 10 wherein circuit topology of the transceiver is configured to provide contemporaneous reporting of neural signals received from the sensors when external stimulation is provided between electrodes of the plurality of electrodes.

13. The system of claim 10 wherein the system monitor is configured to receive the contemporaneous neural signals from the transceiver and to record the received contemporaneous neural signals.

14. The system of claim 10 wherein the substrate comprises no more than 0.8 mm of medical grade silicone.

15. The system of claim 10 wherein the flexible two-dimensional substrate is in the shape of a polygon.

16. The system of claim 10 wherein the sensors are equidistantly spaced along one-dimensional arrays of the substrate.

17. The system of claim 10 wherein the plurality of open spacings further comprises end recesses between the adjacent arrays of the plurality of arrays.

18. The system of claim 10 wherein at least one cross-member connects the adjacent arrays of the plurality of arrays.

* * * * *